United States Patent

Glisan

[11] Patent Number: 5,816,251
[45] Date of Patent: Oct. 6, 1998

[54] BACK SUPPORT SYSTEM

[76] Inventor: Billy Joe Glisan, 1613 Redberry Ct., Fort Collins, Colo. 80525

[21] Appl. No.: 953,658

[22] Filed: Oct. 17, 1997

[51] Int. Cl.$^6$ ..................................................... A61G 15/00
[52] U.S. Cl. ............................................. 128/845; 602/19
[58] Field of Search ................................... 128/845, 846, 128/869, 870, 874, 875, 876, 882; 602/19, 24

[56] References Cited

U.S. PATENT DOCUMENTS

| | | | |
|---|---|---|---|
| 1,008,500 | 11/1911 | Thornton | 602/19 |
| 1,812,524 | 6/1931 | Haulbrook | 602/19 |
| 3,543,748 | 12/1970 | Charturs | 602/19 |
| 4,541,419 | 9/1985 | Osawa | 602/19 |
| 4,576,151 | 3/1986 | Carmichael | 602/24 |
| 5,135,470 | 8/1992 | Reeves | 602/19 |

*Primary Examiner*—Michael A. Brown
*Attorney, Agent, or Firm*—John E. Toupal; Harold G. Jarcho

[57] ABSTRACT

A back support system including a first cuff for securement around one thigh of an individual; a second cuff for securement around the other thigh of the individual; a suspender harness for securement over the individual's shoulders, the suspender harness having a rear connection portion arranged for placement in substantial transverse alignment with the individual's upper spine, and first and second front connection portions for placement over the individual's chest; and an elastic mechanism attached between the rear connection portion and each of the first and second cuffs, the elastic mechanism having first and second elastic portions extending over, respectively, portions of the individual's buttocks with the first elastic portion being attached to an attachment portion of the first cuff and the second elastic portion being attached to an attachment portion of the second cuff.

20 Claims, 4 Drawing Sheets

BACK SUPPORT SYSTEM

BACKGROUND OF THE INVENTION

This invention relates generally to back support systems and, more particularly, to back support systems for reducing the risk of low back muscle injury typically caused by lifting and bending activities.

Under normal circumstances, as individuals bend over using the low back as a fulcrum to manually lift, handle and lower objects, the mass of the upper body is supported by the muscles of the low back, posterior hips, and hamstrings. As the upper body moves from an upright erect posture towards a forward flexed posture of approximately 90 degrees, the forces required by the low back muscles to support the upper body increase dramatically due to an increased moment arm developed as the mass of the upper body moves forward of the low back fulcrum. Due to this increase in load on the low back muscles and intervertebral disks, the potential for a low back muscle strain, sprain or disk herniation increases dramatically as the upper body bends towards 90 degrees. Additionally, if an individual twists the low back while or after having bent forward, the supporting low back muscles on one side of the spine are placed in a position where they do not support the spine and upper body nearly as effectively as when only forward bending takes place, essentially reducing the ability of the low back muscles to support the mass of the upper body. This factor increases the potential for low back strains and sprains when lifting in a forward flexed, twisted position.

Prior attempts to alleviate low back problems generally have entailed the use of various types of support belts and harnesses. Typical lumbar back support belts traditionally have wrapped around the trunk circumferentially in the transverse plane. Such devices have not, however, provided a satisfactory solution to low back problems caused by lifting and bending activities. Also, potential energy has been used with exercise cords and bands to provide resistance against exercising muscles. However, as related to industrial injury prevention applications, and rehabilitative bracing, sports and conditioning applications, the use of highly elastic rubber material and the generated potential energy have not been utilized successfully to support, accelerate, decelerate or assist the joints and muscles of the body.

Another type of back support system is disclosed in U.S. Pat. No. 1,008,500. That system included a harness arrangement having shoulder and thigh attachments by a narrow, rigid metallic and elongated spring member overlaying a user's spine. The disclosed system lacks flexibility that accommodates three-dimensional body movement and fails to address low back injury associated with body twisting motions. Consequently, the patented system provides less than a complete solution to the problem.

The object of this invention, therefore, is to provide an improved back support system that reduces the risk of low back injuries during lifting, bending and twisting activities.

SUMMARY OF THE INVENTION

The invention is a back support system including a first cuff for securement around one thigh of an individual; a second cuff for securement around the other thigh of the individual; a suspender harness for securement over the individual's shoulders, the suspender harness having a rear connection portion arranged for placement in substantial transverse alignment with the individual's upper spine, and first and second front connection portions for placement over the individual's chest; and an elastic mechanism attached between the rear connection portion and each of the first and second cuffs, the elastic mechanism having first and second elastic portions extending over, respectively, portions of the individual's buttocks with the first elastic portion being attached to a rear attachment portion of the first cuff, and the second elastic portion being attached to a rear attachment portion of the second cuff. The elastic mechanism allows the spine to move through normal motions and movements, statically or dynamically providing support throughout a select range of motion, stretching the band and then utilizing the generated potential energy developed therein to assist the muscles of the low back, posterior hips, hamstrings and other muscles to return the body towards an upright standing position.

According to a specific feature of the invention, the elastic mechanism includes an elastic member attached between the rear connection portion and each of the first and second cuffs, a first strap for extension under one arm of the individual and for connection between the first front connection portion and the attachment portion of one of the first and second cuffs and a second strap for extension under the other arm of the individual and for connection between the second front connection portion and the attachment portion of the other of the first and second cuffs. The first and second straps assist the elastic member in the storage and advantageous release of potential energy.

According to one feature of the invention, the attachment portions of the first and second cuffs are rear portions thereof. This feature enhances function of the system during body twisting movements.

According to another feature of the invention, the one arm is the individual's right arm, the one thigh is the individual's left thigh, and each of the first and second straps is an elastic strap. The elastic straps provide dynamic support and assistance during twisting movement of the body.

In one embodiment of the invention, the elastic band has a triangularly shaped lower portion forming the first and second elastic portions and an elongated upper portion attached between the apex of the triangular portion and the rear connection portion. This band geometry enhances the functional characteristics of the system in the static model.

According to other features of the above embodiment, the first and second connection portions are located at horizontally spaced apart positions over, respectively, left and right outer chest portions of the individual and the suspender harness includes a third strap connecting the first and second connection portions. These features enhance the stability and adjustability of the harness during use of the system.

According to still other features of the above embodiment, the suspender harness further includes fourth and fifth straps extending between the rear connection portion and, respectively, said first and second front connection portions; and a pliable pad secured to a lower portion of each of the fourth and fifth straps. These features enhance stability, comfort and adjustability of the harness.

According to yet other features of the above embodiment, the system includes adjustment mechanisms for adjusting the circumference of each of the first and second cuffs; and the lengths of each of the first, second and third straps; and detachable connectors connecting the first strap to the first front connection portion and the second strap to the second front connection portion. The adjustment mechanisms permit adjustments to accommodate different body sizes and the connectors facilitate assembly of the system on the individual.

According to another embodiment of the invention, the elastic member defines the first and second elastic portions, the first strap is attached to the attachment portion of the one cuff by the second elastic portion, and the second strap is attached to the attachment portion of the other cuff by the first elastic portion. The elastic member and first and second straps allow the spine to move through normal motions and movements, statically or dynamically providing support throughout a select range of motion, stretching the band and then utilizing the generated potential energy developed therein to assist the muscles of the low back, posterior hips, hamstrings and other muscles to return the body towards an upright standing position.

According to one feature of the above embodiment, the elastic member is triangularly shaped with a base portion forming the first and second elastic portions, and an apex attached to the rear attachment portion. This flexible band geometry enhances functional characteristics of the system.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENTS

Figure 1:
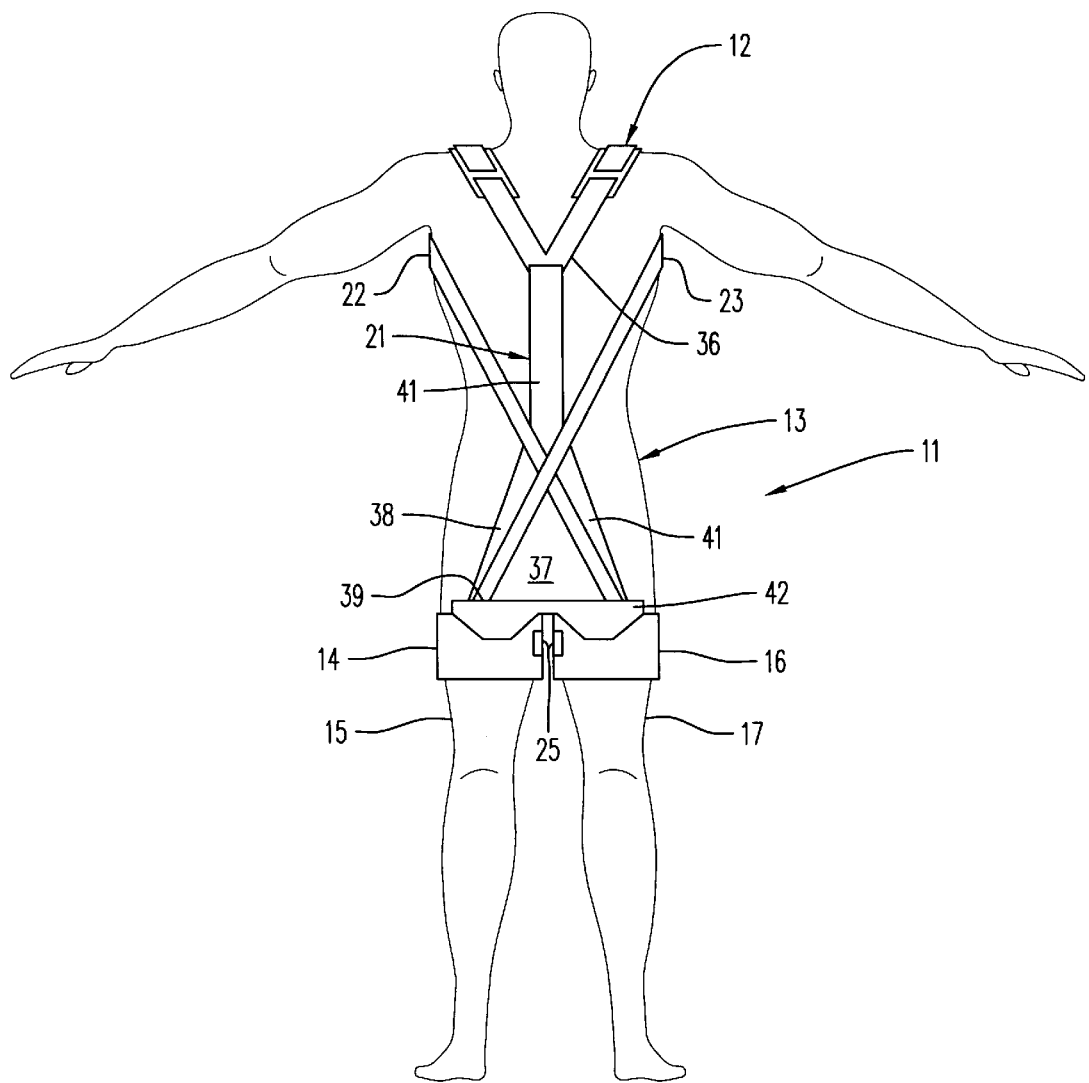
FIG. 1 is a rear view of a back support system secured to a user.
Figure 2:
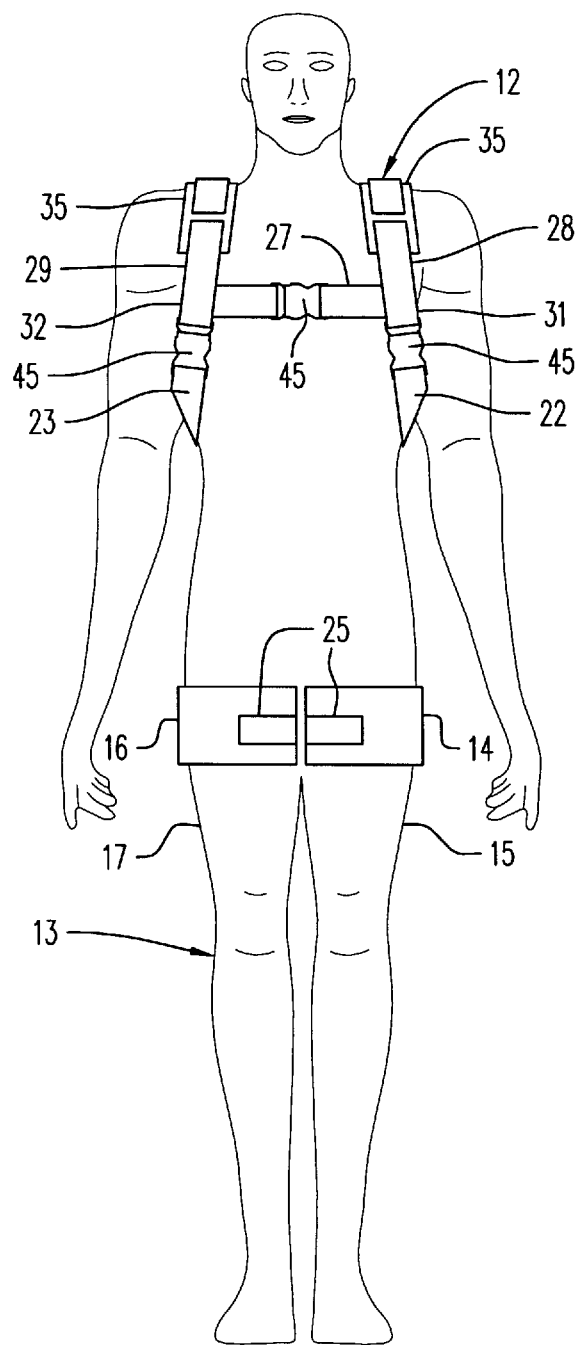
FIG. 2 is a front view of the back support system shown in FIG. 1.

A back support system 11 includes a suspender harness 12 supported by the shoulders of an individual 13, a first cuff 14 secured around one thigh 15 of the individual 13 and a second cuff 16 secured around the other thigh 17 of the individual. Also included in the support system 11 is a non-metallic elastic mechanism including an elastic band member 21 extending between the shoulder harness 12 and the first and second cuffs 14, 16; a first elastic strap 22 extending between the shoulder harness 12 and the second cuff 16; and a second elastic strap 23 extending between the shoulder harness 12 and the first cuff 14. Preferably, the elastic band 21 and the first and second straps 22, 23 are formed of highly elastic material such as rubber. Each of the first and second cuffs 14, 16 are provided with connectors 25 such as Velcro pads which facilitate circumferential length adjustments of the cuffs 14, 16 around, respectively, the thighs 15, 17.

The shoulder harness 12 includes third, fourth and fifth straps 27–29 positioned over, respectively, the chest and shoulders of the individual 13. Joined ends of third and fourth straps 27, 28 form a first front connection portion 31 of the shoulder harness 12 and joined ends of the third and fifth straps 27, 29 form a second front connection portion 32 thereof. A pliable pad 35 is secured to a lower central portion of each of the fourth and fifth straps 28, 29. Joined opposite ends of the fourth and fifth straps 28, 29 form for the shoulder harness 12 a rear connection portion 36 transversely aligned with the upper spine of the individual 13.

The elastic band member 21 has a triangularly shaped lower portion 37, the base of which forms a first elastic portion 38 attached to an outer rear webbing portion 39 of the first cuff 14 and a second elastic portion 41 attached to an outer rear webbing portion 42 of the second cuff 16. As shown in FIG. 1, the first and second elastic portions 38, 39 extend over, respectively, outer portions of the individual's buttocks. An elongated upper portion 41 of the elastic band 21 extends between the apex of the lower band portion 37 and the rear connection portion 36 of the shoulder harness 12.

Figure 3:
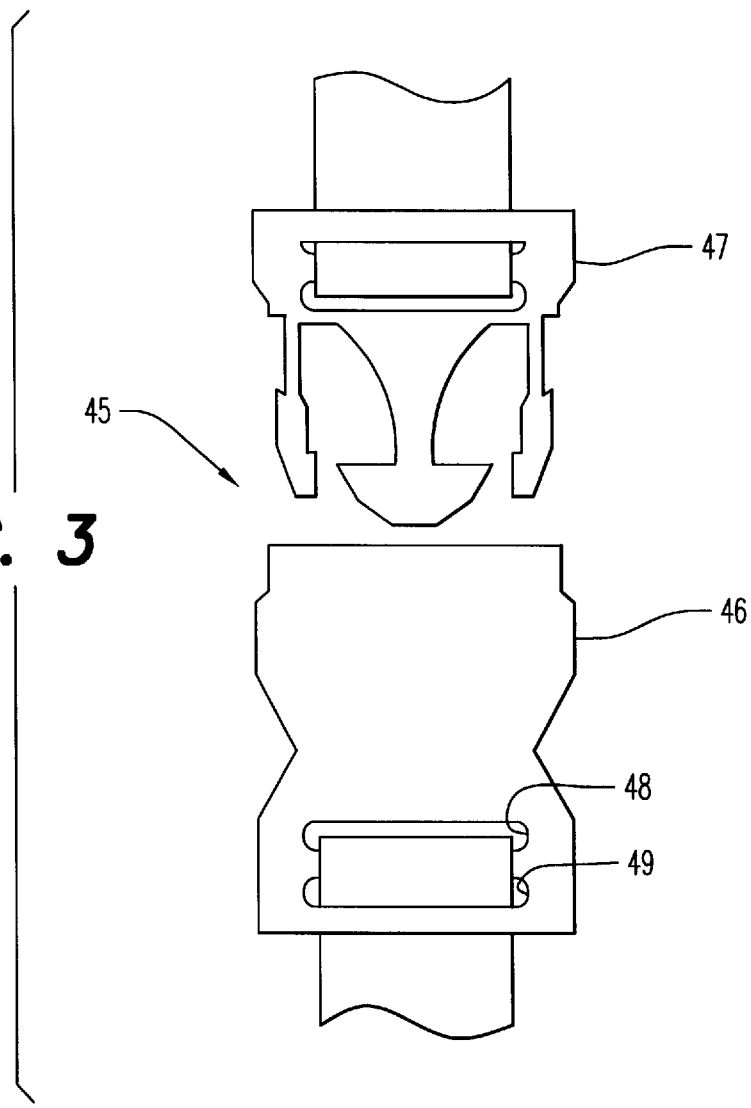
FIG. 3 is an enlarged view of an adjustable connector used in the back support system shown in FIGS. 1 and 2.

The first elastic strap 22 extends under the individual's left arm and has one end attached to the outer rear portion 42 of the second cuff 16 and an opposite end connected to the first front connection portion 31 of the shoulder harness 12 by a detachable connector 45 (FIG. 3). Similarly, the second elastic strap 23 extends under the individual's right arm and has one end attached to the outer rear portion 39 of the first cuff 14 and an opposite end connected to the second front connection portion 32 of the shoulder harness 12 by a detachable connector 45. A detachable connector 45 also connects joined segments of the third strap 27. As shown in FIG. 3, the conventional connector 45 includes a female component 46 which detachably receives a male component 47. Slots 48, 49 in the female component 46 receive ends of the straps 22, 23 and 27 and allow in the conventional manner adjustment in the lengths thereof.

During use of the back support system 11, the elastic band member 21 stretches longitudinally as the individual 13 bends over forward towards the ground from an upright standing position. The band member 21 dynamically supports and transfers a portion of the upper body mass to the thigh cuffs 14 and 16 and legs while mechanically assisting the back muscles to decelerate the velocity of the upper body as it bends forward. In addition, the device 11 can be used to limit how far the low back and spine are allowed to bend. For example, if the individual 13 bends forward until the device 11 limits further bending, the individual can remain in this position while the device statically assists the muscles and ligaments of the back, hips and thighs to support the mass of the upper body. The degree of bending is variable and can be varied by adjustment of the shoulder harness 12. As a further benefit of the device 11, as the individual 13 starts to stand back up from a forward bent position, the potential energy generated in the elastic band 21 pulls on the shoulder harness 12 and upper body to mechanically assist the muscles of the back, hips and thighs to extend the back, hips and knees as the individual stands back up.

To a lesser degree, the first and second elastic straps 22 and 23 assist the elastic band 21 in supporting the mass of the upper body. However, their primary function is to provide support and transfer a portion of the weight of the upper body to the legs through the straps 22 and 23 as the upper body twists while bending forward. For example, when rotating to the right, the first strap 22 attached to the right thigh cuff 16 stretches, and the resistance of the strap provides support to the upper body and transfers a portion of the upper body's mass from the low back musculature to the lower body. As the individual 13 starts to stand back up and derotate the spine and upper body from a bent over twisted position, the potential energy from the first strap 22 assists the individual 13 in rotating the upper body back to a standing erect posture. In a similar manner, the second elastic strap 23 functions to support and assist body rotation to the left.

Figure 4:
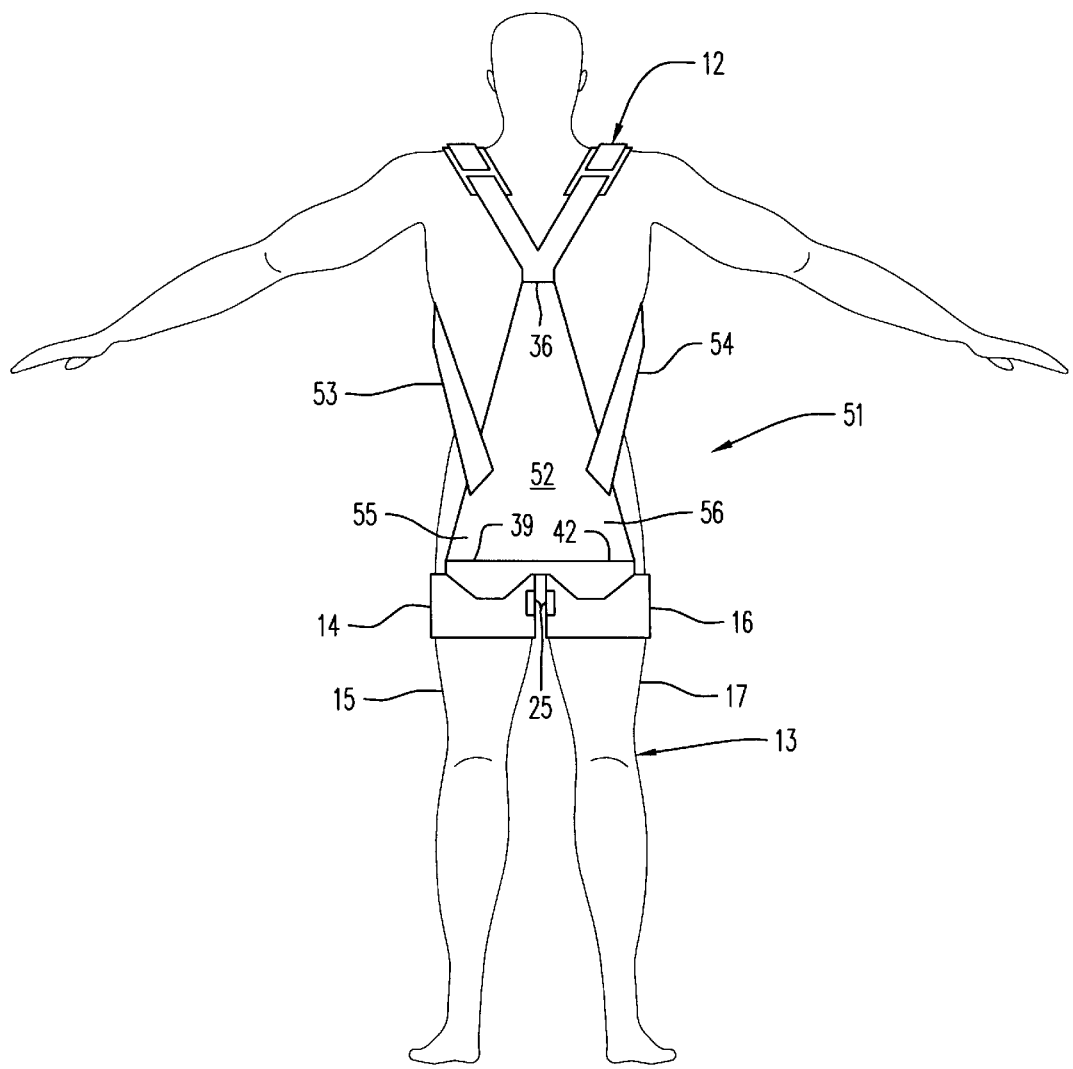
FIG. 4 is a rear view of another back support system embodiment secured to a user.

Another back support system embodiment 51 is illustrated in FIG. 4. Included in the back support system 51 are a shoulder harness 12 and first and second cuffs 14, 16 which are identical to those employed in the embodiment 11 and which have been given corresponding reference numerals. Also included in the back support system 51 is a non-metallic elastic mechanism including a band member 52 extending between the shoulder harness 12 and the first and second cuffs 14, 16; a first webbed strap 53 extending between the shoulder harness 12 and the first cuff 14; and a second webbed strap 54 extending between the shoulder harness 12 and the second cuff 16.

The elastic band member 52 is triangularly shaped with an apex attached to the rear connection portion 36 and a base forming spaced apart first and second elastic portions 55 and 56 attached, respectively, to the outer rear portion 39 of the first cuff 14 and the outer rear portion 42 of the second cuff 16. As shown in FIG. 4, the first and second elastic portions 55, 56 extend over, respectively, outer portions of the individual's buttocks. The first webbed strap 53 extends under the left arm of the individual 13 and has one end attached to the second cuff 16 by the second elastic portion 56 of the elastic band 52. An opposite end of the first webbed strap 53 is connected to the first front connector portion 31 of the shoulder harness 12 by a connector 45. Similarly, the second webbed strap 54 extends under the right arm of the individual 13 and has one end attached to the first cuff 14 by the first elastic portion 55 of the elastic band 52. An opposite end of the second webbed strap 54 is connected to the second front connection portion 32 of the shoulder harness 12 by a connector 45.

During use of the back support system 51, the elastic band 52 functions in the same manner as the elastic band 21 of embodiment 11 to dynamically support and transfer a portion of the upper body mass to the thigh cuffs 14, 16 and legs while mechanically assisting the back muscles to decelerate the velocity of the upper body as it bends forward. In addition, the system 51 can be adjusted as described above to limit bending motion of the back and spine and will provide potential energy to mechanically assist the muscles of the back, hips and thighs to extend the back, hips and knees as the individual returns to a standing position.

Due to the geometry of the elastic band 52 and to the attachment of the first and second straps 53, 54 to outer edges thereof, the elastic band 52 also provides support and transfers a portion of the mass of the upper body as the individual 13 twists while bent over. In that way, the system 51 can limit how far the wearer is allowed to bend and twist the low back and spine while dynamically and statically supporting the mass of the upper body in these positions. As the individual 13 starts to stand back up from a bent over twisted position, the potential energy generated in the elastic band 52 assists the muscles of the low back, hip and thighs once again to extend the hips and low back and to assist the individual to a standing position.

Obviously, many modifications and variations of the present invention are possible in light of the above teachings. For example, the invention can be used on other body parts such as joints to provide stabilization during rehabilitative exercises after an injury. Also, the invention can be utilized in sports and or recreational applications to decrease the work of select muscles while assisting select muscles and the bodies ability to perform select movements or activities. It is to be understood, therefore, that the invention can be practiced otherwise than as specifically described.

What is claimed is:

1. A back support system comprising:
    a first cuff for securement around one thigh of an individual;
    a second cuff for securement around the other thigh of the individual;
    suspender means for securement over the individual's shoulders; said suspender means having a rear connection portion arranged for placement in substantial transverse alignment with the individual's upper spine, and first and second front connection portions for placement over the individual's chest; and
    non-metallic, elastic means attached between said rear connection portion and each of said first and second cuffs; said elastic means comprising first and second elastic portions extending over, respectively, portions of the individual's buttocks; said first elastic portion being attached to an attachment portion of said first cuff, and said second elastic portion being attached to an attachment portion of said second cuff.

2. A back support system according to claim 1 wherein said elastic means comprises:
    an elastic member attached between said rear connection portion and each of said first and second cuffs;
    a first strap for extension under one arm of the individual and for connection between said first front connection portion and said attachment portion of one of said first and second cuffs; and
    a second strap for extension under the other arm of the individual and for connection between said second front connection portion and said attachment portion of the other of said first and second cuffs.

3. A back support system according to claim 2 wherein said attachment portions of said first and second cuffs comprise rear portions thereof.

4. A back support system according to claim 3 wherein said one arm is the individual's left arm and said one thigh is the individual's right thigh.

5. A back support system according to claim 4 wherein each of said first and second straps is an elastic strap.

6. A back support system according to claim 5 wherein said elastic member has a triangularly shaped lower portion forming said first and second elastic portions and an elongated upper portion attached between the apex of said triangularly shaped portion and said rear connection portion.

7. A back support system according to claim 6 wherein said first and second connection portions are located at horizontally spaced apart positions over, respectively, left and right outer chest portions of the individual; and said suspender means includes a third strap connecting said first and second connection portions.

8. A back support system according to claim 7 wherein said suspender means further includes fourth and fifth straps extending between said rear connection portion and, respectively, said first and second front connection portions.

9. A back support system according to claim 8 including a pliable pad secured to a lower portion of each of said fourth and fifth straps.

10. A back support system according to claim 9 including cuff adjustment means for adjusting the circumference of each of said first and second cuffs; and strap adjustment means for adjusting the lengths of each of said first, second and third straps.

11. A back support system according to claim 10 wherein said first and second elastic portions extend over outer left portions of the individual's buttocks.

12. A back support system according to claim 2 wherein said elastic member defines said first and second elastic portions, said first strap is attached to said attachment portion of said one cuff by said second elastic portion, and said second strap is attached to said attachment portion of said other cuff by said first elastic portion.

13. A back support system according to claim 12 wherein said elastic member is triangularly shaped and has a base portion forming said first and second elastic portions, and an apex attached to said rear connection portion.

14. A back support system according to claim 13 wherein said first and second connection portions are located at horizontally spaced apart positions over, respectively, right and left outer chest portions of the individual; and said suspender means includes a third strap connecting said first and second connection portions.

15. A back support system according to claim 14 wherein said suspender means further includes fourth and fifth straps extending between said rear connection portion and, respectively, said first and second front connection portions.

16. A back support system according to claim 15 including a pliable pad to a lower portion of each of said fourth and fifth straps.

17. A back support system according to claim 16 including adjustment means for adjusting the circumference of each of said first and second cuffs; and the lengths of each of said first, second and third straps.

18. A back support system according to claim 17 wherein said attachment portions of said first and second cuff comprise rear portions thereof.

19. A back support system according to claim 12 wherein said attachment portions of said first and second cuffs comprise rear portions thereof.

20. A back support system according to claim 19 wherein said one arm is the individual's left arm and said one thigh is the individual's right thigh.

* * * * *